United States Patent [19]
Ueda et al.

[11] Patent Number: 6,107,511
[45] Date of Patent: Aug. 22, 2000

[54] PROCESS FOR THE PURIFICATION OR ISOLATION OF (2S,3R)-1-HALO-2-HYDROXY-3-(PROTECTED AMINO)4-PHENYLTHIOBUTANES OR OPTICAL ANTIPODES THEREOF

[75] Inventors: Yasuyoshi Ueda, Himeji; Katsuji Maehara, Kobe; Tadashi Sugawa, Akashi; Hiroshi Murao, Takasago; Akira Nishiyama, Kakogawa; Hajime Manabe, Takasago, all of Japan

[73] Assignee: Kaneka Corporation, Osaka, Japan

[21] Appl. No.: 09/269,298

[22] PCT Filed: Jul. 29, 1998

[86] PCT No.: PCT/JP98/03375

§ 371 Date: May 14, 1999

§ 102(e) Date: May 14, 1999

[87] PCT Pub. No.: WO99/06364

PCT Pub. Date: Feb. 11, 1999

[51] Int. Cl.[7] .................................................. C07C 261/00
[52] U.S. Cl. ............................. 560/29; 564/185; 564/341
[58] Field of Search ............................. 560/29; 564/185, 564/341

[56] References Cited

U.S. PATENT DOCUMENTS 5,484,926   1/1996   Dressman et al. .

FOREIGN PATENT DOCUMENTS 9509843   8/1996   WIPO .
9623756   8/1996   WIPO .

*Primary Examiner*—Samuel Barts
*Attorney, Agent, or Firm*—Pollock, Vande Sande & Amernick

[57] ABSTRACT

The present invention has for its object to provide a commercially useful, expedient and efficient method for purification and isolation of an N-protected (2S,3R)-1-halo-2-hydroxy-3-amino-4-phenylthiobutane (1) or its enantiomer, which is capable of removing the various contaminants, particularly said byproducts, whereby the problem of instability of the compound (1) or its enantiomer can be overcome and a high product yield can be insured.

The present invention relates to a method of purifying and isolating an N-protected (2S,3R)-1-halo-2-hydroxy-3-amino-4-phenylthiobutane (1):

(1)

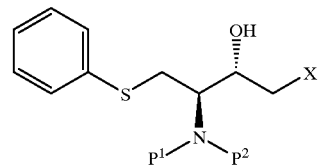

(wherein X represents a halogen atom; one of $P^1$ and $P^2$ represents a hydrogen atom and the other represents an amino-protecting group, or $P^1$ and $P^2$ taken together represents an amino-protecting group) or its enantiomer, which comprises using an aromatic hydrocarbon solvent to remove impurities occurring in said compound (1) or impurities occurring in said enantiomer from said compound (1) containing impurities or its enantiomer containing impurities and isolate said compound (1) or said enantiomer as crystals.

20 Claims, No Drawings

PROCESS FOR THE PURIFICATION OR ISOLATION OF (2S,3R)-1-HALO-2-HYDROXY-3-(PROTECTED AMINO)4-PHENYLTHIOBUTANES OR OPTICAL ANTIPODES THEREOF

TECHNICAL FIELD

The present invention relates to a method of purifying and isolating an N-protected (2S,3R)-1-halo-2-hydroxy-3-amino-4-phenylthiobutane of the following general formula (1) or its enantiomer. The following compound is useful as an intermediate for the production of medicinal compounds, particularly an HIV protease inhibitor (Viracept™ already on the market) which is described inter alia in EP 604185 A1.

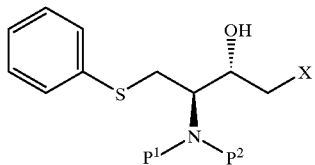

(1)

(wherein X represents a halogen atom; one of $P^1$ and $P^2$ represents a hydrogen atom and the other represents an amino-protecting group, or $P^1$ and $P^2$ taken together represents an amino-protecting group).

PRIOR ART

The N-protected (2S,3R)-1-halo-2-hydroxy-3-amino-4-phenylthiobutane of the above general formula (1) (hereinafter referred to sometimes as Compound (1)) can be synthesized by, for example, the process described in WO 95/09843 or the process described in WO 96/23756 or the like.

In the process according to WO 95/09843, (2R)-2-N-(benzyloxycarbonyl)amino-3-phenylthiopropanoic acid is first converted to (3S)-1-diazo-2-oxo-3-N-(benzyloxycarbonyl)amino- 4-phenylthiobutane, then converted to the haloketone compound (3R)-1-chloro-2-oxo-3-N-(benzyloxycarbonyl)amino-4-phenylthiobutane and, in turn, it is reduced to the (2S,3R)-1-chloro-2-hydroxy-3-N-(benzyloxycarbonyl) amino-4-Phenylthiobutane.

According to the process described in WO 96/23756, a (2R)-2-N-(benzyloxycarbonyl)amino-3-phenylthiopropanoic ester is converted to the haloketone compound (3R)-1-chloro-2-oxo-3-N-(benzyloxycarbonyl) amino-4-phenylthiobutane, and it is then reduced to the (2S,3R)-1-chloro-2-hydroxy-3-N-(benzyloxycarbonyl) amino-4-phenylthiobutane.

The compound (1) thus obtained is not necessarily thermally stable and, moreover, because of the decompositions and side reactions involved in the course of production, the product is liable to contain various contaminants. Particularly, the N-protected (2R,3R)-1-halo-2-hydroxy-3-amino-4-phenylthiobutane of the following general formula (2) (hereinafter referred to sometimes as compound (2)), the N-protected (3R)-1-phenylthio-2-hydroxy-3-amino-4-phenylthiobutane of the following general formula (3) (hereinafter referred to sometimes as compound (3)), and the N-protected (2R,3S)-1-haro-2-hydroxy-3-amino-4-phenylthiobutane of the following general formula (4) (hereinafter referred to sometimes as compound (4)) tend to form in appreciable amounts as the byproducts of the compound (1) and in order that the objective compound of high quality can be obtained, those byproduct impurities must be somehow eliminated.

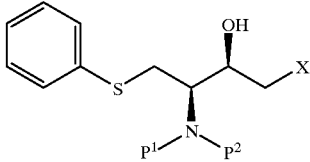

(2)

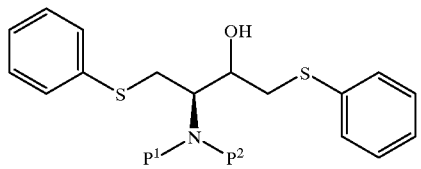

(3)

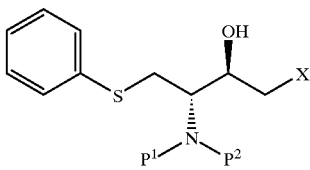

(4)

wherein X, $P^1$ and $P^2$ are defined above.

The above compound (2) is an diastereomer of the objective compound (1) and its byproduction is predicated on the selectivity of reduction of the precursor (haloketone) (3R)-1-halo-2-oxo-3-amino-4-phenylthiobutane.

The above compound (3) is a compound obtained by substitution of a phenylthio group for the 1-halogen atom of the objective compound (1) and its byproduction is apparently attributable to a substitution reaction involving the liberated phenylthio group or its equivalent.

The above compound (4) is an enantiomer of the objective compound (1) and its byproduction is derived from the (S)-formed haloketone which is present with a precursor (haloketone) of the (R)-compound, (3R)-1-halo-2-oxo-3-amino-4-phenylthiobutane and which is an enantiomer thereof. This (S)-formed compound can be produced when the optical purity of (2R)-2-N-(benzyloxycarbonyl)amino-3-phenylthiopropanoic acid or (2R)-2-N-(benzyloxycarbonyl)amino-3-phenylthio-propanoic ester or the like which is a starting material of the methods disclosed in above-mentioned WO95/09843 or WO96/23756 is not entirely high.

As is generally known, it is difficult to remove structurally analogous impurities (related compounds) and in order that such impurities may be removed to provide an objective compound of high quality, there must be established an effective purification and isolation technology.

As the purification and isolation technology of the above compound (1), for example, the process of WO 95/09843 is known, in which the above compound (1) is purified by two runs of flash chromatography ($1^{st}$ run eluent: methanol-containing methylene chloride, $2^{nd}$ run eluent: ethyl acetate-containing chloroform) and then, crystallized from methylene chloride at a very low temperature of −78° C. to isolate it. However, the technology has the following disadvantages.

(1) The objectionable organic solvents (particularly halogenated hydrocarbons such as methylene chloride and chloroform) must be used in large amounts, with the consequent disadvantage associated with the disposal of effluents.
(2) The process is complicated and time-consuming.
(3) The expensive production equipment such as a low-temperature generator is required, which adds to the number of units and capacity of necessary equipment.
(4) A low yield Therefore, this purification and isolation technology has many disadvantages to be overcome for application on a commercial scale.

Thus, the prior art failed to provide an expedient technology for purification and isolation of the above compound (1), which is an objective compound, through efficient removal of said compounds (2), (3), and (4) on a commercial scale. Furthermore, needless to say, any technology for purifying and isolating compound (1) through elimination of compounds (2), (3), and (4) is a technology for purifying and isolating its enantiomer as well.

Under the circumstances, it was a task of extraordinary importance to establish a purification and isolation technology for compound (1) which is a useful intermediate for the production of said HIV protease inhibitor.

SUMMARY OF THE INVENTION

In the light of the states of prior art, the present invention has for its object to provide a commercially useful, expedient and efficient method for purification and isolation of an N-protected (2S,3R)-1-halo-2-hydroxy-3-amino-4-phenylthiobutane (1), which is capable of removing the various contaminants, particularly said compounds (2),(3), and (4) through use of an aromatic hydrocarbon solvent, whereby the problem of instability of the compound (1) can be overcome and a high product yield can be insured.

The present invention relates to a method of purifying and isolating an N-protected (2S,3R)-1-halo-2-hydroxy-3-amino-4-phenylthiobutane of the general formula (1):

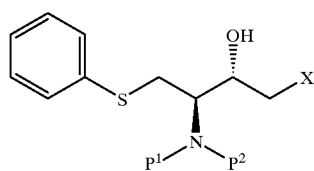

(1)

(wherein X represents a halogen atom; one of $P^1$ and $P^2$ represents a hydrogen atom and the other represents an amino-protecting group, or $P^1$ and $P^2$ taken together represents an amino-protecting group) or its enantiomer, which comprises using an aromatic hydrocarbon solvent to remove impurities occurring in said compound of general formula (1) or impurities occurring in said enantiomer from said compound of general formula (1) containing impurities or its enantiomer containing impurities and isolate said compound of general formula (1) or said enantiomer as crystals.

DETAILED DESCRIPTION OF THE INVENTION

The present invention is now described in detail.

The present invention relates to a method of purifying and isolating the above compound (1) or its enantiomer, which is a method to remove contaminants in the above compound (1) or its enantiomer, and to obtain the above compound (1) or its enantiomer as the crystal from an aromatic hydrocarbon solvent. In the general formula (1), representing the above compound (1), X represents a halogen atom. As above halogen atom, fluorine, chloride, bromide, iodine, or the like can be mentioned, and chloride atom is preferable from the standpoint of the ease of its synthesis. In the general formula (1), one of $P^1$ and $P^2$ represents a hydrogen atom and the other represents an amino-protecting group, or $P^1$ and $P^2$ taken together represent an amino-protecting group. The above amino-protecting group is generally any group that is effective in protecting an amino group. The specific amino-protecting groups which are generally used can be found in academic publications relevant to the particular field, such as Protective Groups in Organic Synthesis (Second Edition, John Wiley & Sons, 1991).

The amino-protecting group that can be used is not particularly restricted, thus including but not limited to benzyloxycarbonyl, methoxycarbonyl, ethoxycarbonyl, tert-butoxycarbonyl, acetyl, trifluoroacetyl, benzyl, dibenzyl, tosyl, phthaloyl, benzoyl, and 3-hydroxy-2-methylbenzoyl (3-hydroxy of which may be protected in the form of e.g. alkoxy or ester). From the standpoint of ease of synthesis of compound (1), urethane type protecting groups such as benzyloxycarbonyl, methoxycarbonyl, ethoxycarbonyl, tert-butoxycarbonyl, etc. are preferred and, among them, benzyloxycarbonyl and tert-butoxycarbonyl are particularly preferred.

The typical impurities occurring in said compound (1) can be removed in accordance with the purification and the isolation of the present invention are (2R,3R)-1-halo-2-hydroxy-3-amino-4-phenylthiobutane (threo-form impurity byproduced at erythro-selective reduction) of above general formula (2), (3R)-1-phenylthio-2-hydroxy-3-amino-4-phenylthiobutane of above general formula (3), and/or (2R, 3S)-1-halo-2-hydroxy-3-amino-4-phenylthiobutane of above general formula (4), which is an enantiomer of the compound (1) (it is derived from (2S)-amino acid isomer which is a contamination of the starting material, an N-protected (2R)-2-N-amino-3-phenylthiopropanoic ester).

Typical impurities occurring in (2R,3S)-form, an enantiomer of above compound (1), which can be removed in accordance with the method of the present invention, are (2S,3S)-1-halo-2-hydroxy-3-amino-4-phenylthiobutane, (3S)-1-phenylthio-2-hydroxy-3-amino-4-phenylthiobutane and/or above compound (1).

The aromatic hydrocarbon solvent used in the method of purifying and isolations of the present invention is not particularly restricted to any single specie but includes compounds of the following general formula (5), among others.

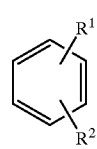

(5)

(wherein $R^1$ and $R^2$ each independently represents a hydrogen atom, a halogen atom, or an alkyl group of 1 to 4 carbon atoms.)

For example, it includes: benzene, toluene, o-xylene, m-xylene, p-xylene, cumene, ethylbenzene, mesitylene, n-butylbenzene, sec-butylbenzene, tert-butylbenzene, p-cymene, o-diethylbenzene, m-diethylbenzene, p-diethylbenzene, chlorobenzene, o-chlorotoluene, m-chlorotoluene, p-chlorotoluene, o-dichlorobenzene, m-dichlorobenzene, and p-dichlorobenzene, etc. Those solvents can be used each alone or in a combination of 2 or more species.

Particularly from the standpoint of the ease of removal of the solvent from the wet compound and the recycle use of the solvent (recovery by distillation), a solvent which has a comparatively low-boiling point is preferred. As such solvent, its boiling point is generally not higher than about 200° C., particularly up to about 150° C., at atmospheric pressure. For example, six membered monocyclic aromatic hydrocarbon solvents of 6 to 9 carbon atoms such as benzene, toluene, o-xylene, m-xylene, p-xylene, cumene, ethylbenzene, and chlorobenzene can be mentioned. From the overall point of view such as cost and safety etc., toluene is particularly preferred.

The use of said aromatic hydrocarbon solvent can lead to stabilization and high yield of said compound (1) and high purification effect, that is to say an effective removal of various impurities, particularly said compound (2), said compound (3), and said compound (4).

The amount of said aromatic hydrocarbon solvent is preferably large enough to maintain fluidity of the system at the end of the procedure for isolating compound (1) as crystals. For example, about 5 to 20 times the weight of compound (1) and, in certain cases, even larger proportions are used. The proper amount of the aromatic hydrocarbon solvent can be easily established by simple experiment.

In the present invention, when isolating above compound (1) as crystals, cooling crystallization or concentrating crystallization or the like, or the combination of these methods can be preferably used. As other methods, so called reslurry process (repulping process) can be used. Furthermore, said concentrating crystallization can be carried out by replacing the solution containing a solvent other than the aromatic hydrocarbon solvents with the solution containing the aromatic hydrocarbon solvent. When isolating above compound (1) as crystals, seed crystals can be added.

In the present invention, when isolating above compound (1) as crystals, an auxiliary solvent other than the aromatic hydrocarbon solvent, for improving at least one condition among the solubility and yield, treating concentration, purification effect (impurity-removing effect), and physical properties of product crystals of compound (1) can be employed. The auxiliary solvent may be added to said aromatic hydrocarbon solvent or used separately.

The auxiliary solvent is not particularly restricted in kind. Thus, it includes but is not limited to acetone, methyl ethyl ketone, tetrahydrofuran, ethyl acetate, isopropyl acetate, acetonitrile, methanol, ethanol, 2-propanol, and methylene chloride etc. Those solvents can be used each alone or in a combination of two or more species. Particularly, by using at least one solvent selected from the group consisting of ethyl acetate, methylene chloride, and acetonitrile, the solubility can be improved and the treating effects such as the treating concentration and the purification effect, etc. can be improved.

The auxiliary solvent can be used with advantage when it is used in combination with said aromatic hydrocarbon solvent in the amount optimized according to the intended effect and its characteristics. Although the quality of the objective compound generally deteriorates when the yield is too large, a proper amount of the auxiliary solvent can be easily established by simple experiment.

From the standpoint of yield and purification effect, the weight ratio of said auxiliary solvent to said aromatic hydrocarbon solvent (the auxiliary solvent/the aromatic hydrocarbon solvent) is preferably not greater than 0.5 at the time of completion of the procedure for isolating the compound of general formula (1) or its enantiomer as crystals. More preferably, a ratio of not greater than 0.3 is used.

The purification and isolation method of the invention can be carried out around room temperature. Where necessary for improving the crystal property or increasing the yield of it, the treatment can be carried out under warming or under cooling, for example at a temperature not over about 60° C., usually at about 50° C. to −20° C. Particularly, said temperature condition is preferably used for inhibiting the decomposition of said compound (1) by heating.

The compound (1) tends to be decomposed in the presence of moisture or oxygen. To minimize this decomposition, the treatment is preferably carried out in an inert gas atmosphere, for example under nitrogen gas, argon gas, or helium gas.

The compound (1) thus obtained is subjected to solid-liquid separation and, where necessary, the cake is washed and dried.

The method for said solid-liquid separation is not particularly restricted but includes pressure-filtration, filtration under reduced pressure, centrifugation, and other techniques.

The preferred method for said drying is drying in vacuo (vacuum drying), for example at a temperature not higher than about 60° C., to avoid pyrolysis. For improving the physical properties and ease of handling of wet crystals, wet crystals can be washed and replaced with a compound which can be used in the practice of the purification and isolation according to the present invention.

In accordance with the present invention, compound (1) can be expediently and efficiently isolated in a yield of not less than 80% and, preferably, not less than 90%.

The purification and isolation method described above can be applied, as it is, to the enantiomer of compound (1) as well.

The above purification and isolation method of the invention is particularly effective in obtaining the objective compound (halohydrin) N-protected (2S,3R)-1-halo-2-hydroxy-3-amino-4-phenylthiobutane or its enantiomer through reduction of the corresponding haloketone compound (3R)-1-halo-2-oxo-3-amino-4-phenylthiobutane or its enantiomer. Particularly the effect of the invention is maximized when the method is applied to the objective compound (halohydrin) rich in impurity which has been produced from the crude haloketone which has not been purified and isolated by crystallization or the like.

Particularly, preferable embodiment of this invention is the crystallization by replacement of a solution which substantially contains a solvent other than the aromatic hydrocarbon solvents (preferably, ethyl acetate etc.) and which contains said compound (1) or its enantiomer, with a solution substantially containing toluene, or the crystallization by cooling a solution substantially containing toluene which contains said compound (1) or its enantiomer (preferably, a solution of toluene containing acetonitorile as the auxiliary solvent, etc.). However, this invention is not limited to these methods.

EXAMPLES

The following examples are intended to illustrate the present invention in further detail and should by no means be construed as defining the scope of the invention.

(Reference Example 1)

Preparation of (2S,3R)-1-chloro-2-hydroxy-3-N-(benzyloxycarbonyl)amino-4-phenylthiobutane Under nitrogen gas, a solution composed of 20.0 g of methyl (2R)-2-N-(benzyloxycarbonyl)amino-3-phenylthiopropanoate, 13.5 g of sodium monochloroacetate, 11.05 g of magnesium chloride, and 80 ml of THF was stirred at 25° C. for 1 hour (Solution A). On the other hand, under nitrogen gas, 23.5 g of diisopropylamine was added to 116 ml of a solution of n-butylmagnesium chloride in THF (2.0 mol/l) over 30 minutes at room temperature and the mixture was further stirred at 50° C. for 1 hour (Solution B). Solution B was added to Solution A over about 1 hour at an internal temperature of about 5° C., and after the completion of the addition, the mixture was stirred for about 10 hours. This mixture was then added to a solution composed of 22.8 g of sulfuric acid, 200 ml of water, and 300 ml of ethyl acetate and the mixture was stirred for 30 minutes to effect hydrolysis. After phase separation, the organic phase was washed serially with 200 ml of water, 200 ml of 5% sodium hydrogencarbonate/$H_2O$, and 200 ml of 1 N-hydrochloric acid and concentrated under reduced pressure.

To 21.6 ml of a solution of DIBAH (diisobutylaluminiumhydride) in toluene (1.02 M) was added 2.64 g of 2-propanol at room temperature, and the mixture was stirred for 1 hour. To this mixture was added the (3R)-1-chloro-2-oxo-3-N-(benzyloxycarbonyl)amino-4-phenylthiobutane equivalent to 3.96 g obtained by concentration under reduced pressure, and the mixture was stirred at room temperature for 3 hours. Then, using 50 ml of 1 N-hydrochloric acid, the hydrolysis reaction was carried out under ice-cooling. This reaction mixture was extracted with 30 ml of ethyl acetate and the extract was washed with 50 ml of 2% sodium hydrogencarbonate/$H_2O$ and 20 ml of 2% NaCl/$H_2O$ in that order and concentrated under reduced pressure. The solvent was replaced with ethyl acetate to provide an ethyl acetate solution containing (2S,3R)-1-chloro-2-hydroxy-3-N-(benzyloxycarbonyl)amino-4-phenylthiobutane. This solution was concentrated to dryness and further dried in vacuo. The quality of the (2S,3R)-1-chloro-2-hydroxy-3-N-(benzyloxycarbonyl)amino-4-phenylthiobutane thus obtained was as follows.
Purity: 79 area % (70 weight %)
(2R,3R)-1-chloro-2-hydroxy-3-N-(benzyloxycarbonyl)amino- 4-phenylthiobutane content: 3.5 area %
(2R,3S)-1-chloro-2-hydroxy-3-N-(benzyloxycarbonyl)amino-4-phenylthiobutane content: 0.2 area %
(3R)-1-phenylthio-2-hydroxy-3-N-(benzyloxycarbonyl)amino-4-phenylthiobutane content: 3.9 area %.

(Reference Example 2)

Preparation of (2S,3R)-1-chloro-2-hydroxy-3-N-(tert-butoxycarbonyl)amino-4-phenylthiobutane Under nitrogen gas, a solution composed of 25.4 g of methyl (2R)-2-N-(tert-butoxycarbonyl)amino-3-phenylthiopropanoate, 14.2 g of sodium monochloroacetic acid, 11.6 g of magnesium chloride, and 20 ml of THF was stirred at 40° C. for 2 hours (Solution A). On the other hand, under nitrogen gas, 44.5 g of diisopropylamine was added to 197 ml of a solution of n-butylmagnesium chloride in THF (1.9 mol/l) over 30 minutes at an internal temperature of 40° C. and the mixture was further stirred at 40° C. for 2 hours (Solution B). Solution B was added to Solution A over about 1 hour at an internal temperature of about –5° C., and after the completion of the addition, the mixture was stirred for about 15 hours. This mixture was added to a solution composed of 81.8 g of concentrated hydrochloric acid, 50 ml of water, and 30 ml of ethyl acetate over 2 hours at 5° C., and the hydrolysis reaction was carried out. After phase separation, the organic phase was washed serially with 200 ml of 5% sodium hydrogencarbonate/$H_2O$ and 200 ml×2 of water and then concentrated under reduced pressure.

To 20.0 ml of a solution (1.02 M) of DIBAH in toluene was added 7.1 g of 2-propanol at room temperature, and the mixture was stirred for 3 hours. To this mixture was added the (3R)-1-chloro-2-oxo- 3-N-(tert-butoxycarbonyl)amino-4-phenylthiobutane equivalent to 2.80 g obtained by concentration under reduced pressure. The mixture was stirred at 5° C. for 10 hours and then added to a solution composed of 1.8 g of concentrated hydrochloric acid, 10 ml of water, and 20 ml of ethyl acetate over 1 hour under ice-cooling. The mixture was further stirred for 13 hours to effect hydrolysis. After hydrolysis, the organic phase was washed with 15 ml of 5% sodium hydrogencarbonate/$H_2O$ and 15 ml of water in 3 cycles and then concentrated under reduced pressure. The solvent was replaced with ethyl acetate to provide an ethyl acetate solution containing (2S,3R)-1-chloro-2-hydroxy-3-N-(tert-butoxycarbonyl)amino-4-phenylthiobutane. This solution was concentrated to dryness and further dried in vacuo. The quality of the (2S,3R)-1-chloro-2-hydroxy-3-N-(tert-butoxycarbonyl)amino-4-phenylthiobutane thus obtained was as follows.
Purity: 85 area % (80 weight %)
(2R,3R)-1-chloro-2-hydroxy-3-N-(tert-butoxycarbonyl)amino-4-phenylthiobutane content: 3.8 area %
(2R,3S)-1-chloro-2-hydroxy-3-N-(tert-butoxycarbonyl)amino-4-phenylthiobutane content: 0.2 area %
(3R)-1-phenylthio-2-hydroxy-3-N-(tert-butoxycarbonyl)amino-4-phenylthiobutane: 3.7 area %

(Reference Example 3)

Preparation of (2R,3S)-1-chloro-2-hydroxy-3-N-(benzyloxycarbonyl)amino-4-phenylthiobutane Using methyl (2S)-2-N-(benzyloxycarbonyl)amino-3-phenylthiopropanoate in lieu of methyl (2R)-2-N-(benzyloxycarbonyl)amino-3-phenylthiopropanoate, the procedure of Reference Example 1 was otherwise repeated to provide an ethyl acetate solution containing (2R,3S)-1-chloro-2 -hydroxy-3-N-(benzyloxycarbonyl)amino-4-phenylthiobutane. This solution was concentrated to dryness and further dried in vacuo. The quality of the (2R,3S)-1-chloro-2-hydroxy-3-N-(benzyloxycarbonyl)amino-4-phenylthiobutane thus obtained was as follows.
Purity: 78 area % (70 weight %)
(2S,3S)-1-chloro-2-hydroxy-3-N-(benzyloxycarbonyl)amino-4-phenylthiobutane content: 4.6 area %
(2S,3R)-1-chloro-2-hydroxy-3-N-(benzyloxycarbonyl)amino-4-phenylthiobutane content: 0.2 area %
(3S)-1-phenylthio-2-hydroxy-3-N-(benzyloxycarbonyl)amino-4-phenylthiobutane content: 4.0 area %

(Example 1)

Under nitrogen gas, 29.9 g of a solution containing 5.44 g of (2S,3R)-1-chloro-2-hydroxy-3-N-(benzyloxycarbonyl)amino-4-phenylthiobutane in toluene/acetonitrile (9:1 (wt/wt)) was cooled from an initial internal temperature of 50° C. under vigorous stirring (treating concentration 18% (weight of solute/weight of solution)). The cooling schedule was 40 minutes down to an internal temperature of 40° C., addition of seed crystals, and 30 minutes of incubation at an internal temperature of 40° C. The resultant slurry was cooled to an internal temperature of 5° C. over 12 hours and incubated at this internal temperature of 5° C. for 2 hours.

The resultant crystal crop was filtered under reduced pressure, drained thoroughly, and washed 3 times with 13 ml each of toluene. The crystals were then dried invacuo (about 1 to 10 mmHg, 20 to 40° C., about 10 hours) to provide 4.32 g (yield 80%) of (2S,3R)-1-chloro-2-hydroxy-3-N-(benzyloxycarbonyl)amino-4 -phenylthiobutane as crystals.

The quality of the (2S,3R)-1-chloro-2-hydroxy-3-N-(benzyloxycarbonyl)amino-4-phenylthiobutane before treatment (after the concentration to dryness and drying in vacuo) was as follows.
Purity: 74 area % (70 weight %)
(2R,3R)-1-chloro-2-hydroxy-3-N-(benzyloxycarbonyl) amino-4-phenylthiobutane content: 5.2 area %
(2R,3S)-1-chloro-2-hydroxy-3-N-(benzyloxycarbonyl) amino-4-phenylthiobutane content: 0.3 area %
(3R)-1-phenylthio-2-hydroxy-3-N-(benzyloxycarbonyl) amino-4-phenylthiobutane content: 3.5 area %

The quality of the (2S,3R)-1-chloro-2-hydroxy-3-N-(benzyloxycarbonyl)amino-4-phenylthiobutane crystals after treatment was as follows.
Purity: 98 area % (99 weight %)
(2R,3R)-1-chloro-2-hydroxy-3-N-(benzyloxycarbonyl) amino-4-phenylthiobutane content: less than 0.1 area %
(2R,3S)-1-chloro-2-hydroxy-3-N-(benzyloxycarbonyl) amino-4-phenylthiobutane content: less than 0.1 area %
(3R)-1-phenylthio-2-hydroxy-3-N-(benzyloxycarbonyl) amino-4-phenylthiobutane content: 0.2 area %

(Example 2)

Under nitrogen gas, 40 g of an ethyl acetate solution containing 1.75 g of (2S,3R)-1-chloro-2-hydroxy-3-N-(benzyloxycarbonyl)amino-4-phenylthiobutane was concentrated to 18.0 g under reduced pressure (about 100 mmHg) at an internal temperature of 30 to 40° C. with vigorous stirring. Then, under an internal pressure of 5 to 50 mmHg with vigorous stirring, the concentrate was further distilled with keeping constant volume of the mixture by addition of toluene, and the solvent was replaced until the ethyl acetate content had decreased to 5 weight % (treating concentration 10% (weight of solute/weight of solution)). The pressure was returned to atmospheric with nitrogen, and under nitrogen gas with vigorous stirring, the solution was incubated at 40° C. for 1 hour. Then, the solution was gradually cooled to an internal temperature of 5° C. and incubated at this temperature for 1 hour.

The resultant crystal crop was filtered under reduced pressure, drained thoroughly, washed with 10 ml of toluene, and dried in vacuo (about 1 to 10 mmHg, 20 to 40° C., about 10 hours) to provide 1.59 g (yield 91%) of (2S,3R)-1-chloro-2-hydroxy-3-N-(benzyloxycarbonyl)amino-4-phenylthiobutane as crystals.

The quality of the (2S,3R)-1-chloro-2-hydroxy-3-N-(benzyloxycarbonyl)amino-4-phenylthiobutane before treatment (after the concentration to dryness and drying in vacuo) was as follows.
Purity: 80 area % (71 weight %)
(2R,3R)-1-chloro-2-hydroxy-3-N-(benzyloxycarbonyl) amino-4-phenylthiobutane content: 5.2 area %
(2R,3S)-1-chloro-2-hydroxy-3-N-(benzyloxycarbonyl) amino-4-phenylthiobutane content: 0.2 area %
(3R)-1-phenylthio-2-hydroxy-3-N-(benzyloxycarbonyl) amino-4-phenylthiobutane content: 3.6 area %

The quality of the (2S,3R)-1-chloro-2-hydroxy-3-N-(benzyloxycarbonyl)amino-4-phenylthiobutane crystals after treatment was as follows.
Purity: 98 area % (98 weight %)
(2R,3R)-1-chloro-2-hydroxy-3-N-(benzyloxycarbonyl) amino-4-phenylthiobutane content: 0.1 area %
(2R,3S)-1-chloro-2-hydroxy-3-N-(benzyloxycarbonyl) amino-4-phenylthiobutane content: less than 0.1 area %
(3R)-1-phenylthio-2-hydroxy-3-N-(benzyloxycarbonyl) amino-4-phenylthiobutane content: 0.5 area %

(Example 3)

Except that o-xylene was used in lieu of toluene, the procedure of Example 2 was otherwise repeated (treating concentration 9% (weight of solute/weight of solution), ethyl acetate content 0 weight %) to provide 1.49 g (yield 85%) of crystals of (2S,3R)-1-chloro-2-hydroxy-3-N-(benzyloxycarbonyl)amino-4-phenylthiobutane.

The quality of the (2S,3R)-1-chloro-2-hydroxy-3-N-(benzyloxycarbonyl)amino-4-phenylthiobutane before treatment (after the concentration to dryness and drying in vacuo) was as follows.
Purity: 78 area % (69 weight %)
(2R,3R)-1-chloro-2-hydroxy-3-N-(benzyloxycarbonyl) amino-4-phenylthiobutane content: 3.9 area %
(2R,3S)-1-chloro-2-hydroxy-3-N-(benzyloxycarbonyl) amino-4-phenylthiobutane content: 0.2 area %
(3R)-1-phenylthio-2-hydroxy-3-N-(benzyloxycarbonyl) amino-4-phenylthiobutane content: 3.9 area %

The quality of the (2S,3R)-1-chloro-2-hydroxy-3-N-(benzyloxycarbonyl)amino-4-phenylthiobutane crystals after treatment was as follows.
Purity: 98 area % (98 weight %)
(2R,3R)-1-chloro-2-hydroxy-3-N-(benzyloxycarbonyl) amino-4-phenylthiobutane content: 0.2 area %
(2R,3S)-1-chloro-2-hydroxy-3-N-(benzyloxycarbonyl) amino-4-phenylthiobutane content: less than 0.1 area %
(3R)-1-phenylthio-2-hydroxy-3-N-(benzyloxycarbonyl) amino-4-phenylthiobutane content: 0.8 area %

(Example 4)

Using ethylbenzene in lieu of toluene, the procedure of Example 2 was otherwise repeated (treating concentration 7% (weight of solute/weight of solution), ethyl acetate content 1 weight %) to provide 1.40 g (yield 80%) of crystals of (2S,3R)-1-chloro-2-hydroxy-3-N-(benzyloxycarbonyl) amino-4-phenylthiobutane.

The quality of the (2S,3R)-1-chloro-2-hydroxy-3-N-(benzyloxycarbonyl)amino-4-phenylthiobutane before treatment (after the concentration to dryness and drying in vacuo) was as follows.
Purity: 80 area % (72 weight %)
(2R,3R)-1-chloro-2-hydroxy-3-N-(benzyloxycarbonyl) amino-4-phenylthiobutane content: 3.7 area %
(2R,3S)-1-chloro-2-hydroxy-3-N-(benzyloxycarbonyl) amino-4-phenylthiobutane content: 0.2 area %
(3R)-1-phenylthio-2-hydroxy-3-N-(benzyloxycarbonyl) amino-4-phenylthiobutane content: 4.0 area %

The quality of the (2S,3R)-1-chloro-2-hydroxy-3-N-(benzyloxycarbonyl)amino-4-phenylthiobutane crystals after treatment was as follows.
Purity: 99 area % (98 weight %)
(2R, 3R)-1-chloro-2-hydroxy-3-N-(benzyloxycarbonyl) amino-4-phenylthiobutane content: 0.2 area %
(2R,3S)-1-chloro-2-hydroxy-3-N-(benzyloxycarbonyl) amino-4-phenylthiobutane content: less than 0.1 area %
(3R)-1-phenylthio-2-hydroxy-3-N-(benzyloxycarbonyl) amino-4-phenylthiobutane content: 0.7 area %

(Example 5)

Using chlorobenzene in lieu of toluene, the procedure of Example 2 was otherwise repeated (treating concentration 10% (weight of solute/weight of solution), ethyl acetate content 3 weight %) to provide 1.42 g (yield 81%) of crystals of (2S,3R)-1-chloro-2-hydroxy-3-N-(benzyloxycarbonyl) amino-4-phenylthiobutane.

The quality of the (2S,3R)-1-chloro-2-hydroxy-3-N-(benzyloxycarbonyl)amino-4-phenylthiobutane before treatment (after the concentration to dryness and drying in vacuo) was as follows.

Purity: 81 area % (73 weight %)
(2R,3R)-1-chloro-2-hydroxy-3-N-(benzyloxycarbonyl)amino-4-phenylthiobutane content: 3.4 area %
(2R,3S)-1-chloro-2-hydroxy-3-N-(benzyloxycarbonyl)amino-4-phenylthiobutane content: 0.3 area %
(3R)-1-phenylthio-2-hydroxy-3-N-(benzyloxycarbonyl)amino-4-phenylthiobutane content: 3.8 area %

The quality of the (2S,3R)-1-chloro-2-hydroxy-3-N-(benzyloxycarbonyl)amino-4-phenylthiobutane crystals after treatment was as follows.
Purity: 99 area % (98 weight %)
(2R,3R)-1-chloro-2-hydroxy-3-N-(benzyloxycarbonyl)amino-4-phenylthiobutane content: 0.1 area %
(2R,3S)-1-chloro-2-hydroxy-3-N-(benzyloxycarbonyl)amino-4-phenylthiobutane content: less than 0.1 area %
(3R)-1-phenylthio-2-hydroxy-3-N-(benzyloxycarbonyl)amino-4-phenylthiobutane content: 0.3 area %

(Example 6)

Using benzene in lieu of toluene and methylene chloride in lieu of ethyl acetate, the procedure of Example 2 was otherwise repeated (treating concentration 8% (weight of solute/weight of solution), methylene chloride content 0 weight %) to provide 1.44 g (yield 82%) of crystals of (2S,3R)-1-chloro-2-hydroxy-3-N-(benzyloxycarbonyl)amino-4-phenylthiobutane.

The quality of the (2S,3R)-1-chloro-2-hydroxy-3-N-(benzyloxycarbonyl)amino-4-phenylthiobutane before treatment (after the concentration to dryness and drying in vacuo) was as follows.
Purity: 79 area % (70 weight %)
(2R,3R)-1-chloro-2-hydroxy-3-N-(benzyloxycarbonyl)amino-4-phenylthiobutane content: 3.5 area %
(2R,3S)-1-chloro-2-hydroxy-3-N-(benzyloxycarbonyl)amino-4-phenylthiobutane content: 0.2 area %
(3R)-1-phenylthio-2-hydroxy-3-N-(benzyloxycarbonyl)amino-4-phenylthiobutane content: 3.9 area %

The quality of the (2S,3R)-1-chloro-2-hydroxy-3-N-(benzyloxycarbonyl)amino-4-phenylthiobutane crystals after treatment was as follows.
Purity: 98 area % (98 weight %)
(2R,3R)-1-chloro-2-hydroxy-3-N-(benzyloxycarbonyl)amino-4-phenylthiobutane content: 0.1 area %
(2R,3S)-1-chloro-2-hydroxy-3-N-(benzyloxycarbonyl)amino-4-phenylthiobutane content: less than 0.1 area %
(3R)-1-phenylthio-2-hydroxy-3-N-(benzyloxycarbonyl)amino-4-phenylthiobutane content: 0.5 area %

(Example 7)

Under nitrogen gas, 70 g of a solution containing 2.21 g of (2S,3R)-1-chloro-2-hydroxy-3-N-(tert-butoxycarbonyl)amino-4-phenylthiobutane in ethyl acetate was concentrated to 40 g under reduced pressure (about 100 mmHg) at an internal temperature of 30 to 40° C. with vigorous stirring. Then, under vigorous stirring, the solvent was distilled off under an internal pressure of 50 to 150 mmHg with the liquid volume being held constant by addition of toluene until the ethyl acetate content had reached 3 weight % (treating concentration 6% (weight of solute/weight of solution)). Then, the pressure was returned to atmospheric with nitrogen gas and the mixture was incubated at 40° C. with vigorous stirring under nitrogen for 1 hour. The mixture was then cooled gradually to an internal temperature of 5° C. and further incubated at this temperature for 1 hour.

The resultant crystals were filtered under reduced pressure, drained thoroughly, and washed with 10 ml of toluene. This crystal crop was dried in vacuo (about 1 to 10 mmHg, 20 to 40° C., about 10 hours) to provide 1.76 g (yield 80%) of crystals of (2S,3R)-1-chloro-2-hydroxy-3-N-(tert-butoxycarbonyl)amino-4-phenylthiobutane.

The quality of the (2S,3R)-1-chloro-2-hydroxy-3-N-(tert-butoxycarbonyl)amino-4-phenylthiobutane before treatment (after the concentration to dryness and drying in vacuo) was as follows.
Purity: 85 area % (80 weight %)
(2R,3R)-1-chloro-2-hydroxy-3-N-(tert-butoxycarbonyl)amino-4-phenylthiobutane content: 3.8 area %
(2R,3S)-1-chloro-2-hydroxy-3-N-(tert-butoxycarbonyl)amino-4-phenylthiobutane content: 0.2 area %
(3R)-1-phenylthio-2-hydroxy-3-N-(tert-butoxycarbonyl)amino-4-phenylthiobutane content: 3.7 area %

The quality of the (2S,3R)-1-chloro-2-hydroxy-3-N-(tert-butoxycarbonyl)amino-4-phenylthiobutane crystals after treatment was as follows.
Purity: 99 area % (99 weight %)
(2R,3R)-1-chloro-2-hydroxy-3-N-(tert-butoxycarbonyl)amino- 4-phenylthiobutane content: 0.1 area %
(2R,3S)-1-chloro-2-hydroxy-3-N-(tert-butoxycarbonyl)amino-4-phenylthiobutane content: less than 0.1 area %
(3R)-1-phenylthio-2-hydroxy-3-N-(tert-butoxycarbonyl)amino-4-phenylthiobutane content: 0.5 area %

(Example 8)

Under nitrogen gas, 149.2 g of a solution containing 1.73 g of (2S,3R)-1-chloro-2-hydroxy-3-N-(benzyloxycarbonyl)amino-4-phenylthiobutane in toluene was gradually concentrated to 20.1 g under reduced pressure at an internal temperature of 30 to 40° C. with vigorous stirring (treating concentration 9% (weight of solute/weight of solution)). Then, under nitrogen gas and vigorous stirring, the mixture was incubated at an internal temperature of 40° C., for 1 hour, then cooled gradually to an internal temperature of 5° C., and further incubated at this internal temperature of 5° C. for 1 hour.

The resultant crystals were filtered under reduced pressure, drained thoroughly, and washed with 10 ml of toluene. This crystal crop was dried in vacuo (about 1 to 10 mmHg, 20 to 40° C., about 10 hours) to provide 1.49 g (yield 86%) of crystals of (2S,3R)-1-chloro-2-hydroxy-3-N-(benzyloxycarbonyl)amino-4-phenylthiobutane.

The quality of the (2S,3R)-1-chloro-2-hydroxy-3-N-(benzyloxycarbonyl)amino-4-phenylthiobutane before treatment (after the concentration to dryness and drying in vacuo) was as follows.
Purity: 79 area % (70 weight %)
(2R,3R)-1-chloro-2-hydroxy-3-N-(benzyloxycarbonyl)amino-4-phenylthiobutane content: 3.5 area %
(2R,3S)-1-chloro-2-hydroxy-3-N-(benzyloxycarbonyl)amino-4-phenylthiobutane content: 0.2 area %
(3R)-1-phenylthio-2-hydroxy-3-N-(benzyloxycarbonyl)amino-4-phenylthiobutane content: 3.9 area %

The quality of the (2S,3R)-1-chloro-2-hydroxy-3-N-(benzyloxycarbonyl)amino-4-phenylthiobutane crystals after treatment was as follows.
Purity: 98 area % (98 weight %)
(2R,3R)-1-chloro-2-hydroxy-3-N-(benzyloxycarbonyl)amino-4-phenylthiobutane content: 0.2 area %
(2R,3S)-1-chloro-2-hydroxy-3-N-(benzyloxycarbonyl)amino-4-phenylthiobutane content: less than 0.1 area %
(3R)-1-phenylthio-2-hydroxy-3-N-(benzyloxycarbonyl)amino-4-phenylthiobutane content: 0.7 area %

(Example 9)

Using (2R,3S)-1-chloro-2-hydroxy-3-N-(benzyloxycarbonyl)amino-4-phenylthiobutane in lieu of (2S,3R)-1-chloro-2-hydroxy-3-N-(benzyloxycarbonyl) amino-4-phenylthiobutane, the procedure of Example 2 was otherwise repeated (treating concentration 10% (weight of solute/weight of solution), ethyl acetate content: 0 weight %) to provide 1.60 g (yield 91%) of crystals of (2R,3S)-1-chloro-2-hydroxy-3-N-(benzyloxycarbonyl)amino-4-phenylthiobutane.

The quality of the (2R,3S)-1-chloro-2-hydroxy-3-N-(benzyloxycarbonyl)amino-4-phenylthiobutane before treatment (after the concentration to dryness and drying in vacuo) was as follows.
Purity: 78 area % (70 weight %)
(2S,3S)-1-chloro-2-hydroxy-3-N-(benzyloxycarbonyl) amino-4-phenylthiobutane content: 4.6 area %
(2S,3R)-1-chloro-2-hydroxy-3-N-(benzyloxycarbonyl) amino-4-phenylthiobutane content: 0.2 area %
(3S)-1-phenylthio-2-hydroxy-3-N-(benzyloxycarbonyl) amino-4-phenylthiobutane content: 4.0 area %

The quality of the (2R,3S)-1-chloro-2-hydroxy-3-N-(benzyloxycarbonyl)amino-4-phenylthiobutane crystals after treatment was as follows.
Purity: 98 area % (98 weight %)
(2S,3S)-1-chloro-2-hydroxy-3-N-(benzyloxycarbonyl) amino-4-phenylthiobutane content: 0.2 area %
(2S,3R)-1-chloro-2-hydroxy-3-N-(benzyloxycarbonyl) amino-4-phenylthiobutane content: less than 0.1 area %
(3S)-1-phenylthio-2-hydroxy-3-N-(benzyloxycarbonyl) amino-4-phenylthiobutane content: 0.7 area %

(Example 10)

The crystalline (2S,3R)-1-chloro-2-hydroxy-3-N-(benzyloxycarbonyl)amino-4-phenylthiobutane obtained in Example 2 was treated as in Example 1 (treating concentration 20% (weight of solute/weight of solution), toluene/acetonitrile (3:1, wt/wt)). The yield of the (2S,3R)-1-chloro-2-hydroxy-3-N-(benzyloxycarbonyl)amino-4-phenylthiobutane thus obtained was 91% and the quality of the product crystals was as follows.
Purity: 100 area % (100 weight %)
(2R,3R)-1-chloro-2-hydroxy-3-N-(benzyloxycarbonyl) amino-4-phenylthiobutane content: less than 0.1 area %
(2R,3S)-1-chloro-2-hydroxy-3-N-(benzyloxycarbonyl) amino-4-phenylthiobutane content: less than 0.1 area %
(3R)-1-phenylthio-2-hydroxy-3-N-(benzyloxycarbonyl) amino-4-phenylthiobutane content: less than 0.1 area %

(Example 11)

Under nitrogen gas, 19.2 g of a solution containing 3.66 g of (2S,3R)-1-chloro-2-hydroxy-3-N-(benzyloxycarbonyl) amino-4-phenylthiobutane in toluene/acetonitrile (9:1(wt/wt)) was cooled from an initial internal temperature of 50° C. under vigorous stirring (treating concentration 19% (weight of solute/weight of solution)). The cooling process was 1 hour down to an internal temperature of 40° C., and 30 minutes of incubation at an internal temperature of 40° C. The resultant slurry was cooled to an internal temperature of 5° C. over 12 hours and incubated at this internal temperature of 5° C. for 2 hours.

The resultant crystal crop was filtered under reduced pressure, drained thoroughly, and washed once with 16 ml of toluene. The crystals were then dried in vacuo (about 1 to 10 mmHg, 20 to 40° C., about 10 hours) to provide 3.29 g (yield 90%) of (2S,3R)-1-chloro-2-hydroxy-3-N-(benzyloxycarbonyl)amino-4-phenylthiobutane as crystals.

The quality of the (2S,3R)-1-chloro-2-hydroxy-3-N-(benzyloxycarbonyl)amino-4-phenylthiobutane before treatment (after the concentration to dryness and drying in vacuo) was as follows.
Purity: 98 area % (97 weight %)
(2R,3R)-1-chloro-2-hydroxy-3-N-(benzyloxycarbonyl) amino-4-phenylthiobutane content: 0.2 area %
(2R,3S)-1-chloro-2-hydroxy-3-N-(benzyloxycarbonyl) amino-4-phenylthiobutane content: 1.5 area %
(3R)-1-phenylthio-2-hydroxy-3-N-(benzyloxycarbonyl) amino-4-phenylthiobutane content: 0.7 area %

The quality of the (2S,3R)-1-chloro-2-hydroxy-3-N-(benzyloxycarbonyl)amino-4-phenylthiobutane after treatment was as follows.
Purity: 99 area % (98 weight %)
(2R,3R)-1-chloro-2-hydroxy-3-N-(benzyloxycarbonyl) amino-4-phenylthiobutane content: less than 0.1 area %
(2R,3S)-1-chloro-2-hydroxy-3-N-(benzyloxycarbonyl) amino-4-phenylthiobutane content: 0.2 area %
(3R)-1-phenylthio-2-hydroxy-3-N-(benzyloxycarbonyl) amino-4-phenylthiobutane content: less than 0.1 area %

(Example 12)

Under nitrogen gas, 40 g of a solution containing 3.46 g of (2S,3R)-1-chloro-2-hydroxy-3-N-(benzyloxycarbonyl) amino-4-phenylthiobutane in ethyl acetate was concentrated to 27.8 g under reduced pressure (about 100 mmHg) at an internal temperature of 30 to 40° C. with vigorous stirring. Then, under vigorous stirring, the solvent was distilled off under an internal pressure of 5 to 50 mmHg with the liquid volume being held constant by addition of chlorobenzene until the ethyl acetate content had reached 18 weight % (treating concentration 13% (weight of solute/weight of solution)). Then, the pressure was returned to atmospheric with nitrogen gas and the mixture was incubated at 40° C. with vigorous stirring under nitrogen for 1 hour. The mixture was then cooled gradually to an internal temperature of 5° C. and further incubated at this temperature for 1 hour.

The resultant crystals were filtered under reduced pressure, drained thoroughly, and washed with 15 ml of chlorotoluene once. This crystal crop was dried in vacuo (about 1 to 10 mmHg, 20 to 40° C., about 10 hours) to provide 3.11 g (yield 90%) of crystals of (2S,3R)-1-chloro-2-hydroxy-3-N-(benzyloxycarbonyl)amino-4-phenylthiobutane.

The quality of the (2S,3R)-1-chloro-2-hydroxy-3-N-(benzyloxycarbonyl)amino-4-phenylthiobutane before treatment (after the concentration to dryness and drying in vacuo) was as follows.
Purity: 98 area % (97 weight %)
(2R,3R)-1-chloro-2-hydroxy-3-N-(benzyloxycarbonyl) amino-4-phenylthiobutane content: 0.2 area %
(2R,3S)-1-chloro-2-hydroxy-3-N-(benzyloxycarbonyl) amino-4-phenylthiobutane content: 1.3 area %
(3R)-1-phenylthio-2-hydroxy-3-N-(benzyloxycarbonyl) amino-4-phenylthiobutane content: 0.7 area %

The quality of the (2S,3R)-1-chloro-2-hydroxy-3-N-(bezyloxycarbonyl)amino-4-phenylthiobutane after treatment was as follows.
Purity: 99 area % (98 weight %)
(2R,3R)-1-chloro-2-hydroxy-3-N-(benzyloxycarbonyl) amino-4-phenylthiobutane content: less than 0.1 area %
(2R,3S)-1-chloro-2-hydroxy-3-N-(benzyloxycarbonyl) amino-4-phenylthiobutane content: 0.3 area %
(3R)-1-phenylthio-2-hydroxy-3-N-(benzyloxycarbonyl) amino-4-phenylthiobutane content: less than 0.1 area %

(Comparative Example 1)

One hundred grams (100 g) of a solution containing 2.15 g of (2S,3R)-1-chloro-2-hydroxy-3-N-(benzyloxycarbonyl)

amino-4-phenylthiobutane in methylene chloride was concentrated to 44 g under reduced pressure (about 500 mmHg) at an internal temperature of 20 to 40° C. (treating concentration 5% (weight of solute/weight of solution)). The residue was cooled to an internal temperature of 5° C. and the resultant slurry was further cooled gradually to an internal temperature of −50° C. and maintained at this temperature for 1 hour. This slurry was further cooled to an internal temperature of −76° C. and maintained at the same temperature for 1 hour. The resultant crystal crop was filtered under reduced pressure, drained thoroughly, and washed with 10 ml of cold methylene chloride (about −70° C.). The crystals were dried in vacuo (about 1 to 10 mmHg, 20 to 40° C., about 10 hours) to provide 1.42 g (yield 66%) of crystals of (2S,3R)-1-chloro-2-hydroxy-3-N-(benzyloxycarbonyl) amino-4-phenylthiobutane.

The quality of the (2S,3R)-1-chloro-2-hydroxy-3-N-(benzyloxycarbonyl)amino-4-phenylthiobutane before treatment (after the concentration to dryness and drying in vacuo) was as follows.
Purity: 73 area % (75 weight %)
(2R,3R)-1-chloro-2-hydroxy-3-N-(benzyloxycarbonyl) amino-4-phenylthiobutane content: 3.9 area %
(3R)-1-phenylthio-2-hydroxy-3-N-(benzyloxycarbonyl) amino-4-phenylthiobutane content: 4.0 area %

The quality of the (2S,3R)-1-chloro-2-hydroxy-3-N-(benzyloxycarbonyl)amino-4-phenylthiobutane crystals after treatment was as follows.
Purity: 98 area % (97 weight %)
(2R,3R)-1-chloro-2-hydroxy-3-N-(benzyloxycarbonyl) amino-4-phenylthiobutane content: 0.2 area %
(3R)-1-phenylthio-2-hydroxy-3-N-(benzyloxycarbonyl) amino-4-phenylthiobutane content: 0.7 area %

(Comparative Example 2)

Under nitrogen gas, 71 g of a solution containing 1.50 g of (2S,3R)-1-chloro-2-hydroxy-3-N-(benzyloxycarbonyl) amino-4-phenylthiobutane in 2-propanol was gradually concentrated to 10 g under reduced pressure at an internal temperature of about 30 to 40° C. (treating concentration 17% (weight of solute/weight of solution)). After the pressure was returned to atmospheric pressure, 10 ml of water was added and the mixture was incubated for a while under nitrogen gas. The slurry thus obtained was cooled gradually to an internal temperature of 5° C. and incubated at this temperature for 1 hour. The resultant crystal crop was filtered under reduced pressure, drained thoroughly, and washed with 10 ml of 2-propanol/water. The crystals were then dried in vacuo (about 1 to 10 mmHg, 20 to 40° C., about 10 hours) to provide 1.23 g (yield 82%) of crystals of (2S,3R)-1-chloro-2-hydroxy-3-N-(benzyloxycarbonyl) amino-4-phenylthiobutane.

The quality of the (2S,3R)-1-chloro-2-hydroxy-3-N-(benzyloxycarbonyl)amino-4-phenylthiobutane before treatment (after the concentration to dryness and drying in vacuo) was as follows.
Purity: 83 area % (75 weight %)
(2R,3R)-1-chloro-2-hydroxy-3-N-(benzyloxycarbonyl) amino-4-phenylthiobutane content: 3.3 area %
(3R)-1-phenylthio-2-hydroxy-3-N-(benzyloxycarbonyl) amino-4-phenylthiobutane content: 4.0 area %

The quality of the (2S,3R)-1-chloro-2-hydroxy-3-N-(benzyloxycarbonyl)amino-4-phenylthiobutane crystals after treatment was as follows.
Purity: 87 area % (78 weight %)
(2R,3R)-1-chloro-2-hydroxy-3-N-(benzyloxycarbonyl) amino-4-phenylthiobutane content: 2.1 area %
(3R)-1-phenylthio-2-hydroxy-3-N-(benzyloxycarbonyl) amino-4-phenylthiobutane content: 3.9 area %

(Comparative Example 3)

One hundred grams (100 g) of a solution containing 3.21 g of (2S,3R)-1-chloro-2-hydroxy-3-N-(benzyloxycarbonyl) amino-4-phenylthiobutane in methylene chloride was concentrated to 45 g under reduced pressure (about 500 mmHg) at an internal temperature of 20 to 40° C. (treating concentration 7% (weight of solute/weight of solution)). The residue was cooled to an internal temperature of 5° C. and the resultant slurry was further cooled gradually to an internal temperature of −50° C. and maintained at this temperature for 1 hour. This slurry was further cooled to an internal temperature of −78° C. and maintained at the same temperature for 1 hour. The resultant crystal crop was filtered under reduced pressure, drained thoroughly, and washed with 11 ml of cold methylene chloride (about −70° C.). The crystals were dried in vacuo (about 1 to 10 mmHg, 20 to 40° C., about 10 hours) to provide 2.89 g (yield 90%) of crystals of (2S,3R)-1-chloro-2-hydroxy-3-N-(benzyloxycarbonyl) amino-4-phenylthiobutane.

The quality of the (2S,3R)-1-chloro-2-hydroxy-3-N-(benzyloxycarbonyl)amino-4-phenylthiobutane before treatment (after the concentration to dryness and drying in vacuo) was as follows.
Purity: 98 area % (97weight %)
(2R,3R)-1-chloro-2-hydroxy-3-N-(benzyloxycarbonyl) amino-4-phenylthiobutane content: 0.2 area %
(2R,3S)-1-chloro-2-hydroxy-3-N-(benzyloxycarbonyl) amino-4-phenylthiobutane content: 1.2 area %

The quality of the (2S,3R)-1-chloro-2-hydroxy-3-N-(benzyloxycarbonyl)amino-4-phenylthiobutane after treatment was as follows.
Purity: 99 area % (98 weight %)
(2R,3R)-1-chloro-2-hydroxy-3-N-(benzyloxycarbonyl) amino-4-phenylthiobutane content: less than 0.1 area %
(2R,3S)-1-chloro-2-hydroxy-3-N-(benzyloxycarbonyl) amino- 4-phenylthiobutane content: 0.6 area %

INDUSTRIAL APPLICABILITY

Having the above constitution, the purification and isolation method of the invention can be carried out expediently and efficiently on a commercial scale to provide an N-protected (2S,3R)-1-halo-2-hydroxy-3-amino-4-phenylthiobutane or its enantiomer of improved quality in good yield.

What is claimed is:
1. A method of purifying and isolating an N-protected (2S,3R)-1-halo-2-hydroxy-3-amino-4-phenylthiobutane of the general formula (1):

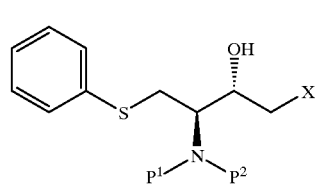

(1)

(wherein X represents a halogen atom; one of $P^1$ and $P^2$ represents a hydrogen atom and the other represents an amino-protecting group, or $P^1$ and $P^2$ taken together represents an amino-protecting group) or its enantiomer, which comprises using an aromatic hydrocarbon solvent to remove an impurity occurring in said compound of general formula (1) or an impurity occurring in said enantiomer from said compound of general formula (1) containing impurities or its enantiomer containing impurities and isolate said compound of general formula (1) or said enantiomer as crystals.

2. A method of purifying and isolating according to claim 1 wherein either cooling crystallization or concentrating crystallization or both are used in isolating the compound as crystals.

3. A method of purifying and isolating an N-protected (2S,3R)-1-halo-2-hydroxy-3-amino-4-phenylthiobutane according to claim 1 wherein the impurity occurring in the compound of general formula (1) is at least one selected from the group consisting of an N-protected (2R,3R)-1-halo-2-hydroxy-3-amino- 4-phenylthiobutane of the general formula (2):

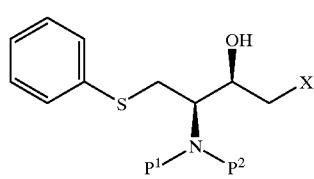

(2)

(wherein X represents a halogen atom; one of $P^1$ and $P^2$ represents a hydrogen atom and the other represents an amino-protecting group, or $P^1$ and $P^2$ taken together represents an amino-protecting group), an N-protected (3R)-1-phenylthio-2-hydroxy-3-amino-4-phenylthiobutane of the general formula (3):

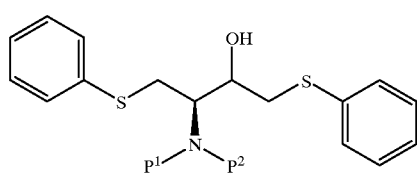

(3)

(wherein $P^1$ and $P^2$ are as defined above), and an N-protected (2R,3S)-1-halo-2-hydroxy-3-amino-4-phenylthiobutane of the general formula (4):

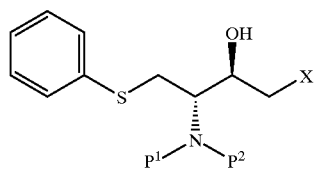

(4)

(wherein X, $P^1$ and $P^2$ are as defined above).

4. A method of purifying and isolating an enantiomer of an N-protected (2S,3R)-1-halo-2 -hydroxy-3-amino-4-phenylthiobutane according to claim 1 wherein the impurity occurring in the enantiomer of the compound of general formula (1) is at least one selected from the group consisting of an N-protected (2S,3S)-1-halo-2-hydroxy-3-amino-4-phenylthiobutane, an N-protected (3S)-1-phenylthio-2-hydroxy-3-amino-4-phenylthiobutane and an N-protected (2S,3R)-1-halo-2-hydroxy-3-amino-4-phenylthiobutane.

5. A method of purifying and isolating according to claim 1, wherein the aromatic hydrocarbon solvent is a compound of the general formula (5):

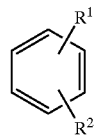

(5)

(wherein $R^1$ and $R^2$ each independently represents a monovalent group selected from the group consisting of a hydrogen atom, a halogen atom, and an alkyl group of 1 to 4 carbon atoms).

6. A method of purifying and isolating according to claim 5 wherein the aromatic hydrocarbon solvent is toluene.

7. A method of purifying and isolating according to claim 1, wherein the isolation as crystals further comprises using an auxiliary solvent in order to improve at least one condition among the solubility, yield, treating concentration, purification effect, and physical properties of crystals of the compound of general formula (1) or its enantiomer.

8. A method of purifying and isolating according to claim 7 wherein the auxiliary solvent is at least one member selected from the group consisting of ethyl acetate, methylene chloride, and acetonitrile.

9. A method of purifying and isolating according to claim 7 wherein the auxiliary solvent is used in such an amount that the weight ratio (said auxiliary solvent/said aromatic hydrocarbon solvent) of the auxiliary solvent to the aromatic hydrocarbon solvent upon completion of the procedure for isolating crystals will be not greater than 0.5.

10. A method of purifying and isolating according to claim 1, wherein the procedure of isolating crystals is performed under an inert gas.

11. A method of purifying and isolating according to claim 1, wherein the amino-protecting group is an urethane-type protective group.

12. A method of purifying and isolating according to claim 11 wherein the amino-protecting group is benzyloxycarbonyl or tert-butoxycarbonyl.

13. A method of purifying and isolating according to claim 1, wherein the halogen atom represented by X in the general formula (1) is chlorine.

14. A method of purifying and isolating an N-protected (2S,3R)-1-halo-2-hydroxy-3-amino-4-phenylthiobutane according to claim 2 wherein the impurity occurring in the compound of general formula (1) is at least one selected from the group consisting of an N-protected (2R,3R)-1-halo-2-hydroxy-3-amino-4-phenylthiobutane of the general formula (2):

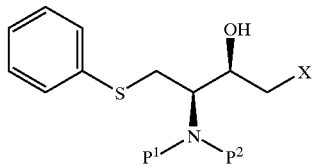

(2)

(wherein X represents a halogen atom; one of $P^1$ and $P^2$ represents a hydrogen atom and the other represents an amino-protecting group, or $P^1$ and $P^2$ taken together represents an amino-protecting group), an N-protected (3R)-1-phenylthio-2-hydroxy-3-amino-4-phenylthiobutane of the general formula (3):

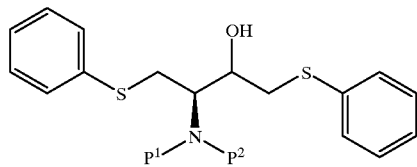 (3)

(wherein $P^1$ and $P^2$ are as defined above), and an N-protected (2R,3S)-1-halo-2-hydroxy-3-amino-4-phenylthiobutane of the general formula (4):

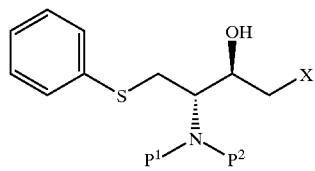 (4)

(wherein X, $P^1$ and $P^2$ are as defined above).

15. A method of purifying and isolating an enantiomer of an N-protected (2S,3R)-1-halo-2-hydroxy-3-amino-4-phenylthiobutane according to claim 2 wherein the impurity occurring in the enantiomer of the compound of general formula (1) is at least one selected from the group consisting of an N-protected (2S,3S)-1-halo-2-hydroxy-3-amino-4-phenylthiobutane, an N-protected (3S)-1-phenylthio-2-hydroxy-3-amino-4-phenylthiobutane and an N-protected (2S,3R)-1-halo-2-hydroxy-3-amino-4-phenylthiobutane.

16. A method of purifying and isolating according to claim 2 wherein the aromatic hydrocarbon solvent is a compound of the general formula (5):

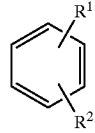 (5)

(wherein $R^1$ and $R^2$ each independently represents a monovalent group selected from the group consisting of a hydrogen atom, a halogen atom, and an alkyl group of 1 to 4 carbon atoms.

17. A method of purifying and isolating according to claim 3 wherein the aromatic hydrocarbon solvent is a compound of the general formula (5):

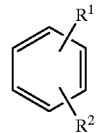 (5)

(wherein $R^1$ and $R^2$ each independently represents a monovalent group selected from the group consisting of a hydrogen atom, a halogen atom, and an alkyl group of 1 to 4 carbon atoms.

18. A method of purifying and isolating according to claim 4 wherein the aromatic hydrocarbon solvent is a compound of the general formula (5):

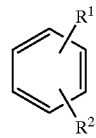 (5)

(wherein $R^1$ and $R^2$ each independently represents a monovalent group selected from the group consisting of a hydrogen atom, a halogen atom, and an alkyl group of 1 to 4 carbon atoms.

19. A method of purifying and isolating according to claim 2 wherein the isolation as crystals further comprises using an auxiliary solvent in order to improve at least one condition among the solubility, yield, treating concentration, purification effect, and physical properties of crystals of the compound of general formula (1) or its enantiomer.

20. A method of purifying and isolating according to claim 3 wherein the isolation as crystals further comprises using an auxiliary solvent in order to improve at least one condition among the solubility, yield, treating concentration, purification effect, and physical properties of crystals of the compound of general formula (1) or its enantiomer.

* * * * *